(12) United States Patent
Viranyi

(10) Patent No.: US 6,299,626 B1
(45) Date of Patent: Oct. 9, 2001

(54) SKIN PRICKER

(76) Inventor: Paul Viranyi, 7 Van Sande Street, Southfield 7800 (ZA)

( * ) Notice: Subject to any disclaimer, the term of this patent is extended or adjusted under 35 U.S.C. 154(b) by 0 days.

(21) Appl. No.: 09/445,138
(22) PCT Filed: Jun. 2, 1998
(86) PCT No.: PCT/US98/11163
  § 371 Date: Jan. 26, 2000
  § 102(e) Date: Jan. 26, 2000
(87) PCT Pub. No.: WO98/55034
  PCT Pub. Date: Dec. 10, 1998

(30) Foreign Application Priority Data

Jun. 2, 1997 (ZA) ...................................... 97/4842
Feb. 6, 1998 (ZA) ...................................... 98/0980

(51) Int. Cl.⁷ .................................................. A61B 17/32
(52) U.S. Cl. ........................................... 606/182; 606/183
(58) Field of Search ................................... 606/181, 182, 606/183, 184, 185, 189; 600/583

(56) References Cited

U.S. PATENT DOCUMENTS

| | | | | |
|---|---|---|---|---|
| 4,677,979 | * | 7/1987 | Burns .................................... | 128/314 |
| 4,991,827 | * | 2/1991 | Taylor .................................... | 267/149 |
| 5,147,375 | | 9/1992 | Sullivan et al. ....................... | 606/182 |
| 5,395,387 | | 3/1995 | Burns .................................... | 606/181 |
| 5,439,473 | | 8/1995 | Jorgensen ............................. | 606/182 |
| 5,540,709 | | 7/1996 | Ramel ................................... | 606/183 |
| 6,062,548 | * | 9/2000 | Nagao et al. .......................... | 267/30 |
| 6,113,620 | * | 9/2000 | Chung ................................... | 606/189 |

FOREIGN PATENT DOCUMENTS 0293092   11/1988   (EP) .

* cited by examiner

Primary Examiner—Michael H. Thaler
(74) Attorney, Agent, or Firm—Ladas & Parry

(57) ABSTRACT

A skin pricker is disclosed which comprises a casing (100) and a plunger (132) which fit together telescopically. To trigger the skin pricker, the plunger's head (134) is placed against the skin to be pricked and the casing (100) pressed towards it. A lancet blade (114) is mounted on an element (112) which is integral with a spring (118). The spring is sinusoidal and includes stops (126, 128, 130) for limiting movement of the "waves" of the spring towards one another. Cams (116) carried by the element (112) co-operate with the end surfaces of plates (138) forming part of the plunger so that during initial movement of the casing, the plunger and element move as a unit. When the stops (126, 128, 130) prevent further movement of the element, the cams urge the plates apart and then enter slots (140) in the plates (138). The spring then forces the blade (114) in a forward skin pricking movement. The cams (116) in the plates (138) and can move freely along the slots. Thus the plunger (132), even if pushed back into the casing (100), cannot recompress the spring (110).

9 Claims, 6 Drawing Sheets

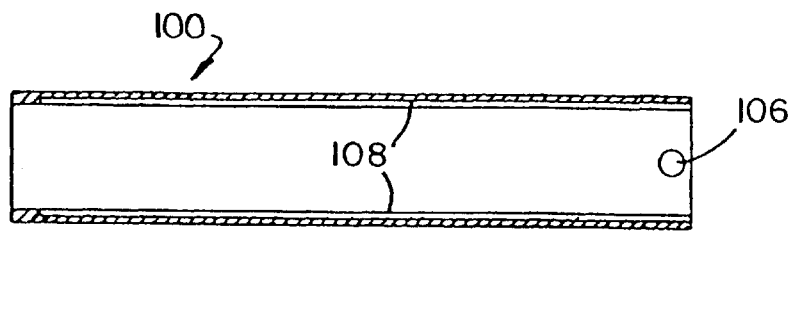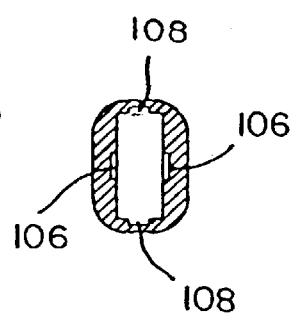
FIG. 9        FIG. 12
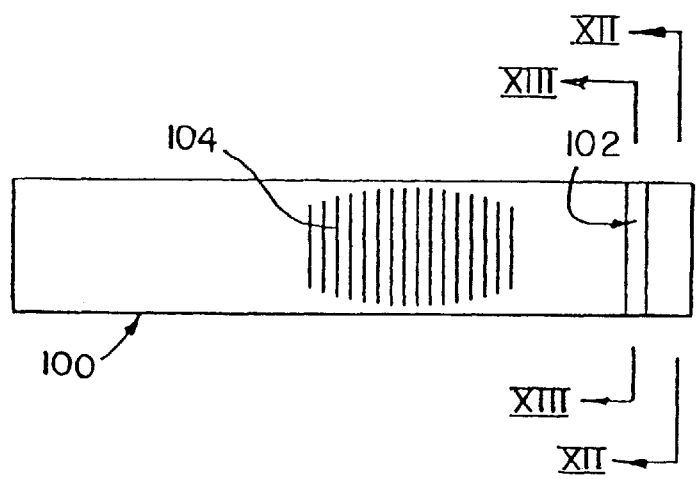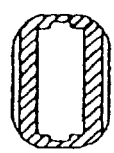
FIG. 10        FIG. 13
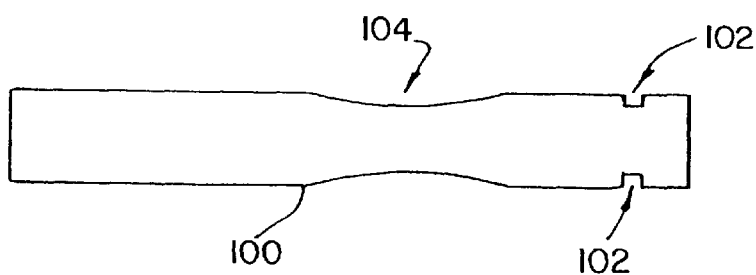
FIG. 11

SKIN PRICKER

FIELD OF THE INVENTION

This invention relates to skin prickers.

BACKGROUND TO THE INVENTION

The need to avoid medical personnel accidentally being cut or pricked by surgical instruments has become of critical importance since the advent of viruses which are transmitted by contaminated blood, and which lead to serious or fatal diseases.

There is now much prior art on this subject and Applicant is aware of US Specifications 5147375, 5611809 and 5487748 which disclose skin prickers having arrangements for rendering them safe after use.

The present invention seeks to provide a skin pricker of improved construction.

BRIEF DESCRIPTION OF THE INVENTION

According to the present invention there is provided a skin pricker having a casing and a plunger which are displaceable with respect to one another when the plunger is placed against the skin to be pricked and the casing is pushed towards the plunger to trigger operation of the skin pricker, the skin pricker further including a lancet blade, a spring acting on the lancet blade for urging the lancet blade in a skin pricking forward stroke and then withdrawing it to an inoperative position, said blade being displaced with respect to the casing by the plunger during an initial part of the relative displacement between the plunger and casing, energy being stored in the spring during such initial movement, and the blade being disconnected from the plunger upon relative movement between said casing and plunger exceeding said initial part thereby to permit the spring to exert itself and urge said blade in said forward stroke relative to the casing and the plunger.

The skin pricker can have stop means for limiting movement of the lancet blade said stop means becoming effective upon said casing completing said initial part of its movement with respect to the plunger.

In the preferred form said spring is of sinusoidal form and includes a series of waves, the spring including stops for limiting closing-up of the waves, said stops constituting said stop means.

To limit the force needed to compress the spring, it can include a series of thinner curved portions joined by thicker generally straight portions.

To improve the prospects of drawing blood said blade can have two points for pricking the skin at two adjacent locations.

In one constructional form said blade is secured to an element which includes at least one shear pin which initially is contacted by a surface of the plunger so that the plunger and element form a unit and the casing moves relatively to this unit, said pin being sheared of by said surface when said stop means becomes effective to limit further movement of said element with respect to the casing thereby to permit the spring to exert itself and urge said blade and element in said forward stroke.

In another constructional form said blade is secured to an element which includes at least one cam which is initially contacted by a surface of the plunger, and is displaced by that surface, so that the plunger and element form a unit and the casing moves relatively to this unit, said surface being on a plate which is resiliently flexible, said cam temporarily camming said plate to a deflected position upon said stop means becoming effective to limit further movement of said element with respect to the casing so that said cam disengages from said surface and the element and blade are free from restraint by the plunger thereby to permit the spring to exert itself and urge said blade and element in said forward stroke.

Said plate desirably has an elongate slot in it which said cam enters and can thereafter move along after camming said plate to its deflected position and disengaging from said surface.

To facilitate assembly, said plunger fits telescopically into an open end of said casing, there being interengaging elongate grooves and latches for preventing said plunger being removed from the casing after insertion whilst permitting relative telescopic movement.

In a specific form said blade is secured to an element which includes at least one cam which is initially contacted by a surface of the plunger, and is displaced by that surface, so that the plunger and element form a unit and the casing moves relatively to this unit, said surface being on a plate which is resiliently flexible, said cam temporarily camming said plate to a deflected position upon said stop means becoming effective to limit further movement of said element with respect to the casing so that said cam disengages from said surface and the element and blade are free from restraint by the plunger thereby to permit the spring to exert itself and urge said blade and element in said forward stroke, said plunger including a head and a parallel spaced pair of said plates protruding from a rear face thereof, said head having an opening in it through which said blade projects during said forward stroke.

According to a further aspect of the present invention there is provided a generally sinusoidal spring having a series of bends joined by a series of generally straight portions, the bends being thinner than the straight portions.

BRIEF DESCRIPTION OF THE DRAWINGS

For a better understanding of the present invention and to show how the same may be carried into effect, reference will now be made, by way of example, to the accompanying drawings in which:

FIG. 9 is a longitudinal section through a further form of skin pricker casing;

FIGS. 10 and 11 are a top plan view and a side elevation of the casing of FIG. 9;

FIG. 12 is a section on the line XII—XII of FIG. 10;

FIG. 13 is a section on the line XIII—XIII of FIG. 10;

DETAILED DESCRIPTION OF THE DRAWINGS

Figure 1:
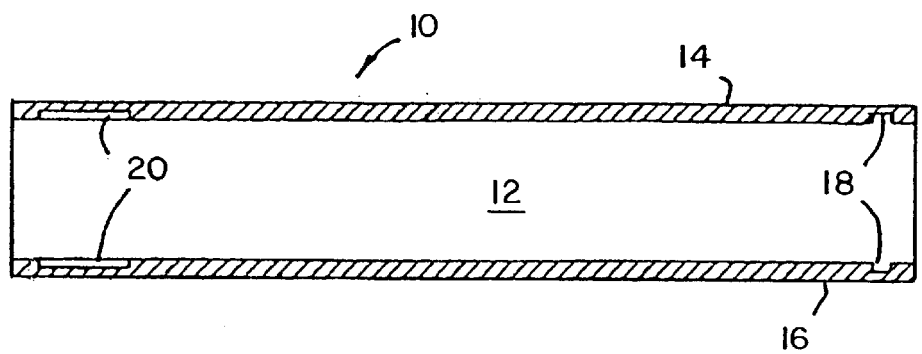
FIG. 1 is a section through one part of a skin pricker casing.

The skin pricker casing part 10 shown in FIG. 1 comprises a main wall 12 which is of elongate rectangular shape. Flanges 14 and 16 (see particularly FIG. 2) protrude from the edges of the wall 12. Each flange 14 and 16 is formed with a narrow groove 18 near the rear end of the casing part and a wider groove 20 near the front end thereof.

Figure 2:
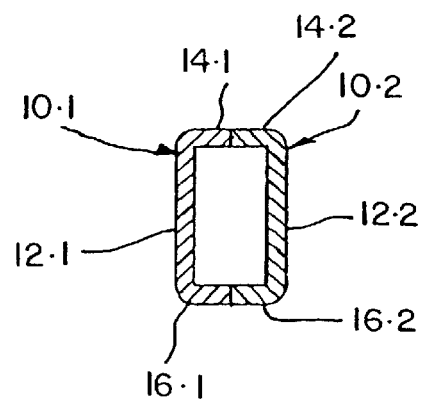
FIG. 2 is a transverse section through a skin pricker casing.

Two casing parts 10, which have been designated 10.1 and 10.2 in FIG. 2, are ultrasonically welded together with the upper and lower flanges 14, 16 abutting to form a casing. In FIG. 2 the flanges are designated 14.1, 14.2, 16.1, 16.2 and the main walls are designated 12.1 and 12.2.

Figure 3:
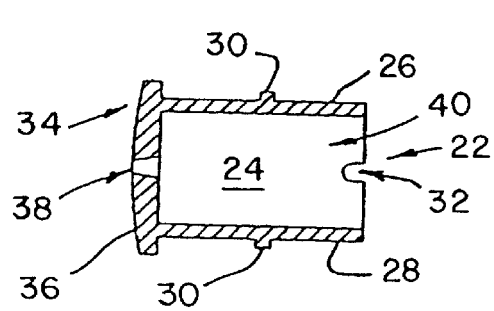
FIG. 3 is a vertical, central cross section through a plunger.

The plunger shown in FIG. 3 is designated 22. It comprises two main walls 24 with upper and lower flanges 26 and 28 spanning between the upper and lower horizontal edges thereof thereby to form a box-like construction. Latches 30 extend upwardly and downwardly from the flanges 26 and 28 and there is a notch 32 in the rear edge of each main wall 24. A front closure structure 34 is provided, this structure comprising a head 36 with an opening 38 in it. The opening 38 narrows in the forward direction, that is, to the left as viewed in FIG. 3. The plunger 22 is thus open at its rear end (the right hand end as viewed in FIG. 3) and has an internal cavity 40. The opening 38 leads into the cavity 40.

Figure 4:
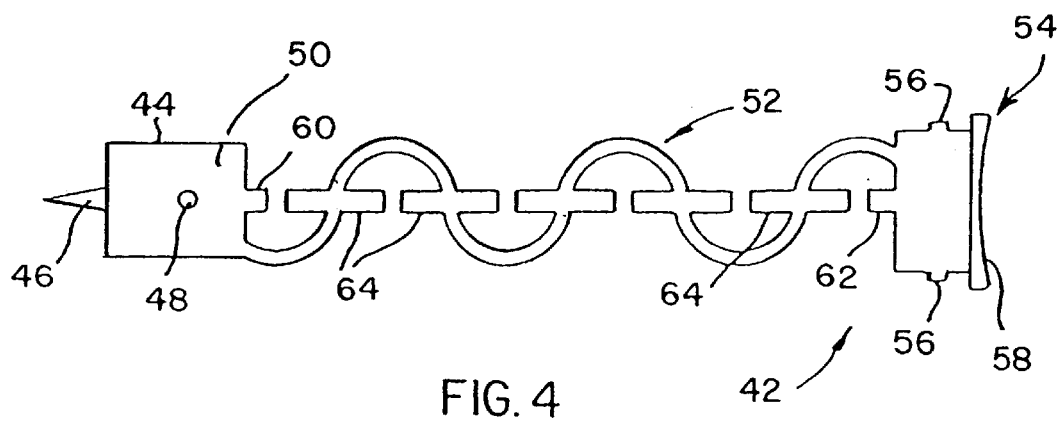
FIG. 4 is an elevation of a spring and lancet blade assembly.

The spring and lancet blade assembly of FIG. 4 is designated 42 and comprises an element 44 which carries a lancet blade 46. The element 44 is of synthetic plastics material and a rear end portion of the blade 46 is moulded into it. Co-axial shear pins 48 protrude from opposed main faces 50 of the element 44 and the element 44 is moulded integrally with a sinusoidal spring 52. At the end of the spring 52 remote from the element 44 there is a plug 54, the spring 52 and plug 54 also being moulded integrally with one another. The plug 54 has two protrusions 56 and a dished rear surface 58 against which thumb pressure can be exerted by the user of the skin pricker.

A stop 60 protrudes rearwardly from the element 44 and a stop 62 protrudes forwardly from the plug 54. The stops are on the "axis" of the spring 52. Further stops 64 protrude forwardly and rearwardly at each point where the "waves" of the spring cross the axis, that is, cross the line joining the centres of the stops 60 and 62. The stops 60, 62 and 64 limit the degree to which the spring 52 can be compressed.

Figure 5:
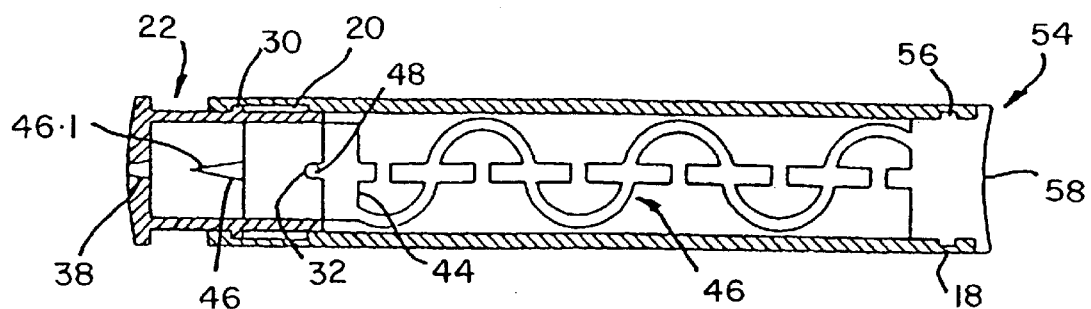
FIGS. 5 to 8 are sections illustrating the manner in which the skin pricker of FIGS. 1 to 4 operates.

To assemble the skin pricker to the condition shown in FIG. 5, the lancet blade 46 and element 44 are entered in the cavity 40 of the plunger 22 through the open rear end thereof. The shear pins 48 enter the notches 32. At this stage the tip of the blade 46 is at the point designated 46.1 in FIG. 5, that is, it is well clear of the opening 38. The structure just described is then placed on the casing part 10.1. The protrusions 56 enter the narrow grooves 18 and this locates the rear end of the structure with respect to the casing part 10. The surface 58 is accessible from externally of the casing. The protrusions 30 enter the elongate grooves 20. The other casing part 10.2 is placed over the casing part 10.1 and the flanges 14.1, 14.2, 16.1, 16.2 welded or glued together. The skin pricker is now as shown in FIG. 5, one end of the skin pricker casing being closed by the plug 54 and the plunger 22 protruding from the other end of the casing. The external transverse dimensions of the plunger 22 are such that it fits in the cavity of the casing which cavity is best seen in FIG. 2.

Figure 6:
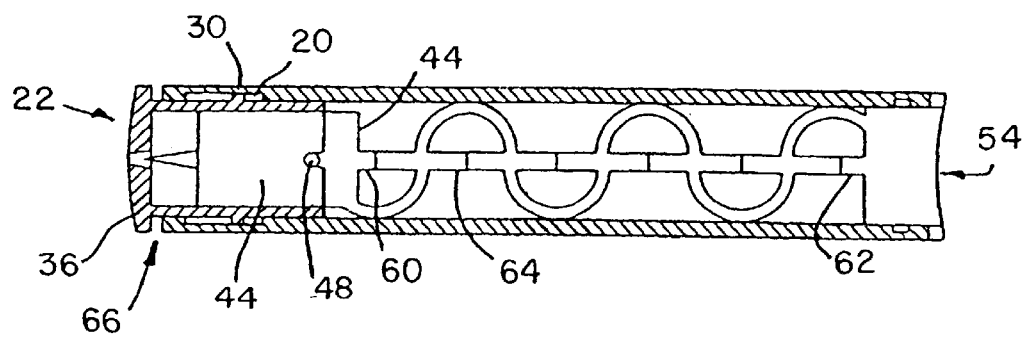

In use of the skin pricker, the casing is gripped and the head 36 of the plunger 22 pressed against the part of the body that is to be penetrated by pressure exerted on the plug 54. This pressure causes the plunger 22 to slide into the casing (see FIG. 6), the protrusions 30 moving along the grooves 20 and the gaps between the stops 60, 62, 64 closing up. These gaps are eliminated before the protrusions 30 reach the rear ends of the grooves 20. The stops now form a solid rod between the element 44 and the plug 54. There is still a slight gap (designated 66 in FIG. 6) between the rear face of the head 36 of the plunger 22 and the front end of the skin pricker casing.

The spring 52 and element 44 are now incapable of further movement and further movement of the plunger 22 has to be accommodated by relative movement between the plunger 22 and the element 44. The pins 48 are thus sheared off by pressure exerted on them by the surfaces bounding the notches 32.

Figure 7:
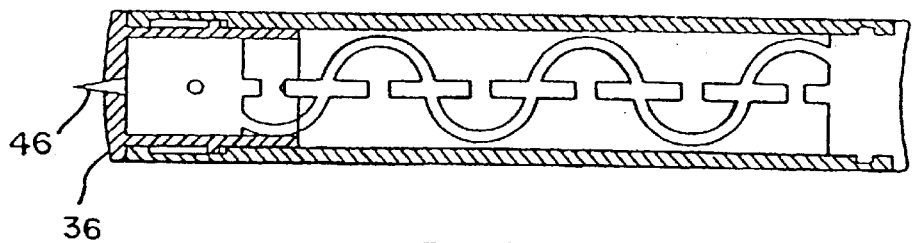

As soon as the pins 48 shear, the connection between the element 44 and the plunger 22 is broken and the spring 52 propels the blade 46 forward to the position shown in FIG. 7. Because the plunger head 36 is pressed against the body part to be penetrated, the plunger 22 does not move with the element 44 and the tip of the blade 46 emerges through the opening 38 and punctures the body part against which the plunger 22 is pressed.

Figure 8:
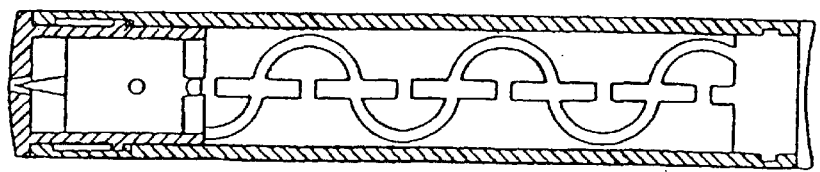

The spring 52 is extended at this time beyond the position it adopts when completely relaxed. As soon as the element 44 hits the inside face of the head 36, the spring recoils and returns to its relaxed condition withdrawing the blade 46 to the position shown in FIG. 8. The blade 46 is entirely within the plunger 22 and inaccessible from outside the skin pricker. Regardless of where the protrusions 30 are in the grooves 20, the blade 46 cannot protrude through the opening 38. Furthermore, it is impossible for the skin pricker to be used again because, in the absence of the pins 48, the spring 42 cannot be re-compressed which is a necessary pre-requisite to urging the blade 46 forward in a penetrating stroke. Thus neither other patients nor staff are in danger of infection from a skin pricker which has already been used.

Turning now to FIGS. 9 to 13, the casing 100 illustrated is of hollow elongate form with a generally rectangular cavity therein (see particularly FIG. 12). The casing 100 is open at both ends and has, close to one end, a pair of external grooves 102 which traverse the major faces of the casing. The major faces also have therein two depressions 104 which are ribbed and facilitate gripping of the casing 100. At one end of the casing there are two internal recesses 106, the recesses being in the inner faces of the two major walls of the casing 100. Two grooves 108 run substantially the full length of the casing. More specifically, each grooves 108 extends from one end of the casing 100 and terminates at a position close to the other end of the casing 100.

Figure 14:
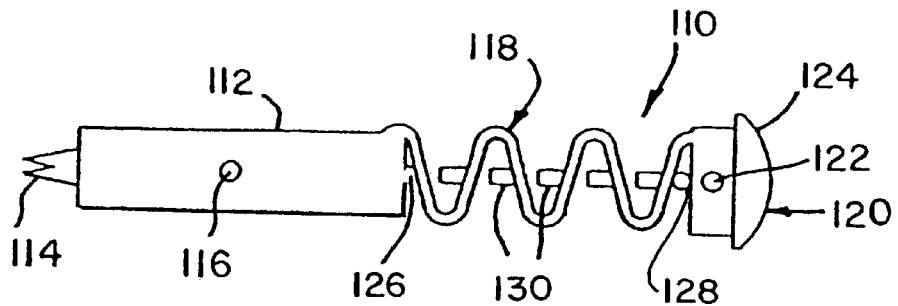
FIGS. 14 and 15 are a side elevation and an underneath plan view of a spring and lancet blade assembly.
Figure 15:
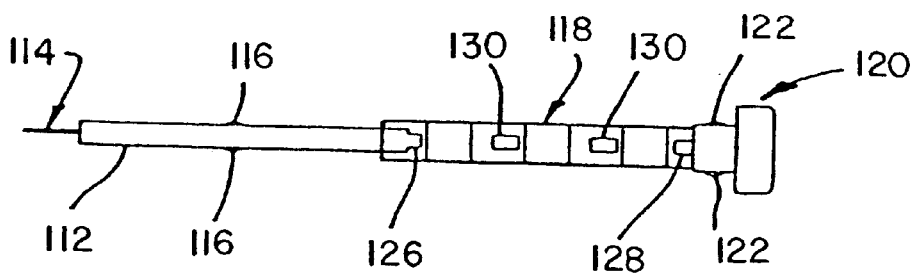

A spring and lancet blade assembly is shown in FIGS. 14 and 15 and is generally designated 110. The assembly 110 comprises an element 112 which has a double pointed lancet blade 114 partially embedded therein and protruding from one end thereof. The element 112 is in the form of an elongate block, there being a cam 116 standing proud of each of the major faces of the block.

The element 112 is moulded integrally with a generally sinusoidal spring 118. The spring 118 is itself moulded integrally with a plug 120. The plug 120 has a protrusion 122 on each face thereof and a dished rear surface 124 against which thumb pressure can be exerted by the user of the skin pricker.

A stop 126 protrudes rearwardly from the element 112 and a stop 128 protrudes forwardly from the plug 120. Further stops 130 protrude forwardly from the spring at each point where the "waves" of the spring cross the main axis. The stops 126, 128 and 130 limit the degree to which the spring 118 can be compressed.

Figure 16:
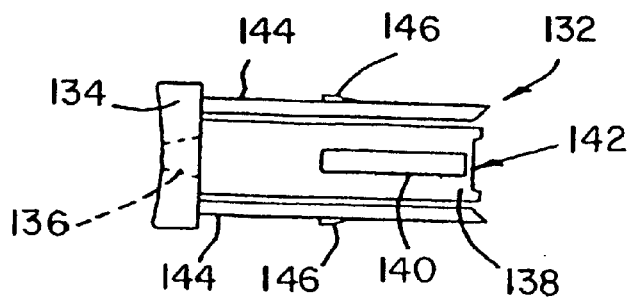
FIG. 16 is a side elevation of a plunger.
Figure 17:
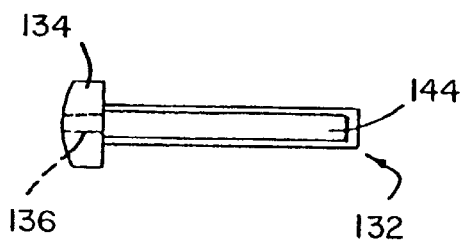
FIG. 17 is a top plan view of the plunger of FIG. 16.

Referring now to FIGS. 16 and 17, the plunger illustrated is generally designated 132 and comprises a head 134 with an opening 136 in it. Protruding from the head 134 are two spaced, thin plates 138 each of which has an elongate slot 140 therein. A notch 142 is formed in the end of each plate 138 remote from the head 134.

Fingers 144 also protrude from the head 134, the fingers 144 substantially closing the upper and lower ends of the gap between the plates 138. A triangular latch 146 protrudes from the outer face of each finger 144.

Figure 18:
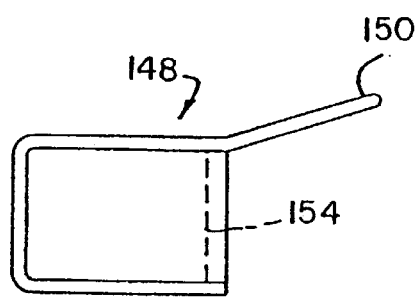
FIG. 18 is a side elevation of a cap.
Figure 19:
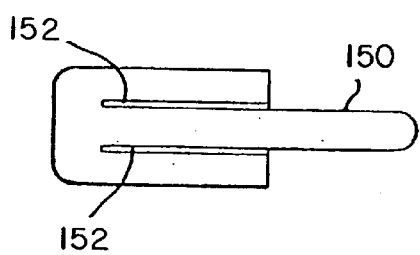
FIG. 19 is a top plan view of the cap of FIG. 18.

The cap shown in FIGS. 18 and 19 is designated 148, is of generally hollow configuration and is open on one side only. A tear-off strip 150 is attached to the remainder of the cap 148 along weakened lines 152.

The entrance to the hollow interior of the cap 150 is bounded, on each of two of the opposed faces thereof, by a protruding rib 154.

Figure 20:
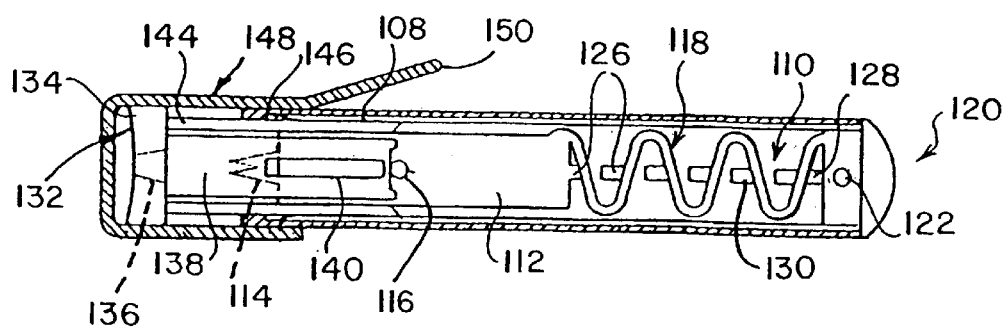
FIG. 20 illustrates an assembled skin pricker.

To assemble the skin pricker, the plunger 132 is inserted through the left hand end of the casing 100 as viewed in FIG. 20, The latches 146 are cammed inwardly by the end portion of the casing which is not provided with grooves 108. Immediately the latches 146 reach the grooves 108 they snap outwardly and enter the grooves. Engagement between those surfaces of the latches 146 which are normal to the fingers 144 and the end faces of the grooves 108 prevents the plunger 132 thereafter being removed from the casing 100. The assembly 110 is inserted through the right hand end of the casing 100 (as viewed in FIG. 20) and pushed in until the protrusions 122 enter the recesses 106. This locks the plug 120 in place and closes-off one end of the casing 100.

As the plunger assembly 110 is inserted into the casing 100, the element 112 passes between the plates 138. The cams 116 of the element 112 enter the notches 142. At this stage the lancet blade 114 is well spaced from the opening 136 in the head 134 and there is no danger that anyone handling the skin pricker will be cut.

The cap 148 is then pushed over the left hand end of the casing 100 until the ribs 154 enter the grooves 102. The cap 148 cannot thereafter be removed from the casing 100 without pulling on the strip 150 to tear the cap 148 along the weakened lines 152 and release the ribs 154 from the grooves 102.

It will be noted that the plunger 132 protrudes from the casing 100 and lies within the cap 148.

Once the cap 148 has been removed as described, the plunger 132 is accessible. It is placed on the part of the body that is to be punctured. The casing 100, gripped by means of the depressions 104, is pushed towards said body part. This causes the plunger 132 to move into the casing 100, the protrusions 116, and hence the element 112, being pushed back by the plunger 132 and the latches 146 sliding along the grooves 108. The spring 118 compresses until the stops 126, 128 and 130 form a solid "rod" between the element 112 and the plug 120. Once the spring 118 is fully compressed, the element 112 can no longer move with the plunger 132.

Further pressure on the plunger 132 causes relative movement between the plunger and the element 112. The cams 116 cam the plates 138 apart and the cams 116, upon further relative movement between the plunger 132 and the element 112 occurring, enter the slots 140.

The compressed spring 118 is then able to force the element 112 to the left as it is no longer restrained by the plunger 132. The blade 114 emerges through the opening 136 and penetrates the body part. The spring 118 at this time has moved beyond its relaxed condition. It then recoils to its relaxed condition withdrawing the blade 114 to a position within the plunger 132.

Because the head 134 is now against the end of the casing 100, the plunger 132 cannot be pushed any further into the casing 100 which movement might expose the blade 114. Furthermore, even if the plunger 132 is withdrawn from the casing 100 to the full extent allowed by the latches 146, and then pushed back into the casing, the spring 118 is not compressed because there is no longer any connection between the plunger 132 and the element 112, the cams 116 simply sliding along the slots 140.

Figure 21:
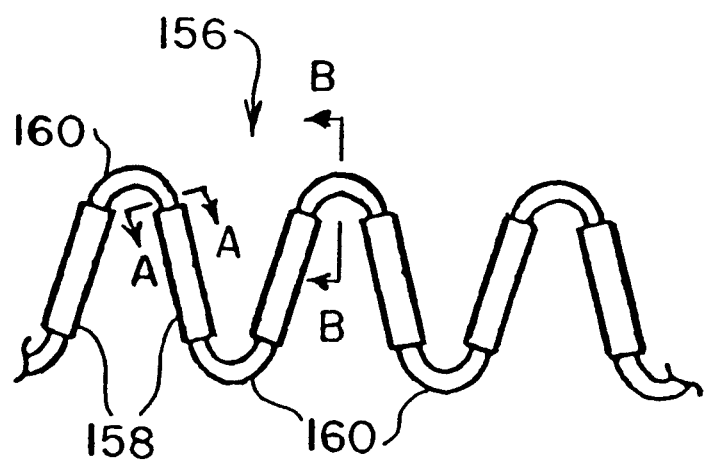
FIG. 21 is a side view of a further form of spring.
Figure 22:
FIGS. 22 and 23 are sections on the lines XII—XII and XIII—XIII in FIG. 21.
Figure 23:
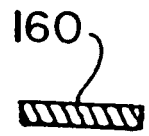

The spring 156 shown in FIGS. 21, 22 and 23 is intended for use in the skin prickers of FIGS. 1 to 8 and of FIGS. 9 to 20 and replaces the springs 52 and 118. It is moulded using synthetic plastics material and comprises a series of thicker portions 158 and a series of thinner portions 160, the thicker portions 158 and thinner portions 160 alternating with one another.

The crests and troughs of the "waves" of the spring 156 are constituted by the thinner portions 160.

Because the crests and troughs of the spring are constituted by the thinner portions 160, and it is the thinner portions 160 that bend when the spring 156 is compressed or tensioned, the force needed to compress or tension the spring is less than would be needed had the entire spring been of the thickness of the portions 158.

The provision of the thinner portions 160 ensures that relatively low forces applied to the skin prickers are sufficient to compress the spring. If the thinner portions 160 had the same cross-section as the thicker portions 158, an unacceptably large force would be required to compress the spring 156.

Neither the stops 64 and 130, nor the components with which the ends of the spring are integral, have been shown in FIG. 21.

What is claimed is:

1. A skin pricker comprising:

a casing having an open end;

a plunger which protrudes from said open end of the casing and which is free to slide into said casing when the plunger is placed against the skin area to be pricked and the casing is pushed towards said skin area;

a skin pricking lancet blade within said casing;

a spring for displacing said lancet blade in a skin pricking stroke and having a relaxed condition and a condition in which energy is stored therein;

disconnectable means interconnecting said plunger and said lancet blade so that the blade moves with the plunger as the plunger slides into the casing, such motion of the lancet blade with the plunger storing energy in the spring;

stop means for interrupting movement of said lancet blade with the plunger before the plunger has reached the end of its travel with respect to the casing, firther movement of the plunger with respect to the lancet blade disconnecting said blade from the plunger so that the energy stored in the spring urges said blade in a skin pricking stroke with respect to the plunger and casing.

2. A skin pricker as claimed in claim 1, wherein said spring is of sinusoidal form and includes a series of waves, the spring including stops for limiting closing-up of the waves, said stops constituting said stop means.

3. A skin pricker as claimed in claim 2, wherein said spring includes a series of thinner curved portions joined by thicker generally straight portions.

4. A skin pricker as claimed in claim 1, wherein said blade has two points for pricking the skin at two adjacent locations.

5. A skin pricker as claimed in claim 1, wherein said blade is secured to an element which includes at least one shear pin which initially is contacted by a surface of the plunger so that the plunger and element form a unit and the casing moves relatively to this unit, said pin being sheared of by said surface when said stop means becomes effective to limit further movement of said element with respect to the casing thereby to permit the spring to exert itself and urge said blade and element in said forward stroke.

6. A skin pricker as claimed in claim 1, wherein said blade is secured to an element which includes at least one cam which is initially contacted by a surface of the plunger, and is displaced by that surface, so that the plunger and element form a unit and the casing moves relatively to this unit, said surface being on a plate which is resiliently flexible, said cam temporarily camming said plate to a deflected position upon said stop means becoming effective to limit further movement of said element with respect to the casing so that said cam disengages from said surface and the element and blade are free from restraint by the plunger thereby to permit the spring to exert itself and urge said blade and element in said forward stroke.

7. A skin pricker as claimed in claim 1, wherein said blade is secured to an element which includes at least one cam which is initially contacted by a surface of the plunger, and is displaced by that surface, so that the plunger and element form a unit and the casing moves relatively to this unit, said surface being on a plate which is resiliently flexible, said cam temporarily camming said plate to a deflected position upon said stop means becoming effective to limit further movement of said element with respect to the casing so that said cam disengages from said surface and the element and blade are free from restraint by the plunger thereby to permit the spring to exert itself and urge said blade and element in said forward stroke, said plate having an elongate slot in it which said cam enters and can thereafter move along after camming said plate to its deflected position and disengaging from said surface.

8. A skin pricker as claimed in claim 1, wherein said plunger fits telescopically into an open end of said casing, there being interengaging elongate grooves and latches for preventing said plunger being removed from the casing after insertion whilst permitting relative telescopic movement.

9. A skin pricker as claimed in claim 1, wherein said blade is secured to an element which includes at least one cam which is initially contacted by a surface of the plunger, and is displaced by that surface, so that the plunger and element form a unit and the casing moves relatively to this unit, said surface being on a plate which is resiliently flexible, said cam temporarily camming said plate to a deflected position upon said stop means becoming effective to limit further movement of said element with respect to the casing so that said cam disengages from said surface and the element and blade are free from restraint by the plunger thereby to permit the spring to exert itself and urge said blade and element in said forward stroke, said plunger including a head and a parallel spaced pair of said plates protruding from a rear face thereof, said head having an opening in it through which said blade projects during said forward stroke.

* * * * *